United States Patent [19]

Bowers et al.

[11] Patent Number: 4,839,344
[45] Date of Patent: Jun. 13, 1989

[54] POLYPEPTIDE COMPOUNDS HAVING GROWTH HORMONE RELEASING ACTIVITY

[75] Inventors: Cyril Y. Bowers, New Orleans, La.; Frank A. Momany, Concord, Mass.; Ching H. Chang; Wayne L. Cody, both of Kingsport, Tenn.; John C. Hubbs, Gray, Tenn.; Charles H. Foster, Kingsport, Tenn.

[73] Assignee: Eastman Kodak Company, Rochester, N.Y.

[21] Appl. No.: 60,877

[22] Filed: Jun. 12, 1987

[51] Int. Cl.$^4$ .................. A61K 37/43; C07K 7/06
[52] U.S. Cl. ........................... 514/16; 530/328; 530/329
[58] Field of Search ............... 530/324, 328, 329; 514/12, 16

[56] References Cited

U.S. PATENT DOCUMENTS

| | | | |
|---|---|---|---|
| 4,061,626 | 12/1977 | Shields | 260/112.5 |
| 4,105,603 | 8/1978 | Vale, Jr. et al. | 260/8 |
| 4,127,517 | 11/1978 | Coy et al. | 260/8 |
| 4,127,518 | 11/1978 | Coy et al. | 260/8 |
| 4,127,519 | 11/1978 | Coy et al. | 260/8 |
| 4,127,520 | 11/1978 | Coy et al. | 260/8 |
| 4,127,521 | 11/1978 | Coy et al. | 260/8 |
| 4,127,522 | 11/1978 | Coy et al. | 260/8 |
| 4,127,523 | 11/1978 | Coy et al. | 260/8 |
| 4,127,524 | 11/1978 | Coy et al. | 260/8 |
| 4,127,525 | 11/1978 | Coy et al. | 260/8 |
| 4,127,526 | 11/1978 | Coy et al. | 260/8 |
| 4,127,527 | 11/1978 | Coy et al. | 260/8 |
| 4,127,528 | 11/1978 | Coy et al. | 260/8 |
| 4,127,529 | 11/1978 | Coy et al. | 260/8 |
| 4,127,530 | 11/1978 | Coy et al. | 260/8 |
| 4,127,531 | 11/1978 | Coy et al. | 260/8 |
| 4,127,532 | 11/1978 | Coy et al. | 260/8 |
| 4,127,533 | 11/1978 | Coy et al. | 260/8 |
| 4,127,534 | 11/1978 | Coy et al. | 260/8 |
| 4,127,535 | 11/1978 | Coy et al. | 260/8 |
| 4,127,536 | 11/1978 | Coy et al. | 260/8 |
| 4,127,537 | 11/1978 | Coy et al. | 260/8 |
| 4,127,538 | 11/1978 | Coy et al. | 260/8 |
| 4,127,539 | 11/1978 | Coy et al. | 260/8 |
| 4,127,540 | 11/1978 | Coy et al. | 260/8 |
| 4,127,541 | 11/1978 | Coy et al. | 260/8 |
| 4,139,504 | 2/1979 | Coy et al. | 260/8 |
| 4,178,284 | 12/1979 | Sarantakis | 260/112.5 |
| 4,211,693 | 7/1980 | Rivier et al. | 260/112.5 |
| 4,223,019 | 9/1980 | Momany | 424/177 |
| 4,223,020 | 9/1980 | Momany | 424/177 |
| 4,223,021 | 9/1980 | Momany | 424/177 |
| 4,224,316 | 9/1980 | Momany | 424/177 |
| 4,226,857 | 10/1980 | Momany | 424/177 |
| 4,228,155 | 10/1980 | Momany | 424/177 |
| 4,228,156 | 10/1980 | Momany | 424/177 |
| 4,228,157 | 10/1980 | Momany | 424/177 |
| 4,228,158 | 10/1980 | Momany | 424/177 |
| 4,312,857 | 1/1982 | Coy et al. | 424/177 |
| 4,316,891 | 2/1982 | Guillemin et al. | 424/177 |
| 4,350,627 | 9/1982 | Castiglione et al. | 260/112.5 |
| 4,372,884 | 2/1983 | Brown et al. | 260/112.5 |
| 4,393,050 | 7/1983 | Vale, Jr. et al. | 424/177 |
| 4,410,512 | 10/1983 | Bowers | 424/177 |
| 4,410,513 | 10/1983 | Momany | 424/177 |
| 4,411,890 | 10/1983 | Momany | 424/177 |
| 4,428,942 | 1/1984 | Rivier et al. | 424/177 |
| 4,491,541 | 1/1985 | Castiglione et al. | 260/112.5 |
| 4,505,897 | 3/1985 | Coy et al. | 514/11 |
| 4,508,711 | 4/1985 | Coy et al. | 514/11 |
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |

*Primary Examiner*—Delbert R. Phillips
*Attorney, Agent, or Firm*—S. E. Reiter; William P. Heath, Jr.

[57] ABSTRACT

Disclosed are novel polypeptide compounds which promote the release and elevation of growth hormone levels in the blood of animals. Also disclosed are methods of promoting the release and elevation of growth hormone levels in the blood of animals using the disclosed polypeptide compounds.

6 Claims, No Drawings

POLYPEPTIDE COMPOUNDS HAVING GROWTH HORMONE RELEASING ACTIVITY

This invention relates to novel polypeptide compounds which promote the release of growth hormone when administered to animals. In another aspect, this invention relates to methods for promoting the release and elevation of growth hormone levels in animals by administration of specified growth hormone releasing polypeptide compounds thereto.

BACKGROUND OF THE INVENTION

It has been established in the scientific literature that the elevation of growth hormone levels in mammals upon administration of GH-releasing compounds can lead to enhanced body weight and to enhanced milk production if sufficiently elevated GH levels occur upon administration (c.f., P. K. Baker, et al., *J. Animal Science* 59 (supplement 1), 220 (1984): W. J. Croom et al., *J. Dairy Sci.* 67 (supplement 1), 109 (1984): S. N. McCutcheon et al., *J. Dairy Sci*, 67, 2881 (1984)). Further, it is known that the elevation of growth hormone levels in mammals can be accomplished by application of known growth hormone releasing agents, such as the naturally occurring growth hormone releasing hormones disclosed by P. Brazeau et al., *Proc. Natl. Acad. Sci.* 79, 7909 (1982), and M. O. Thorner et al., *Lancet* 1,24 (1983)).

The elevation of growth hormone levels in mammals can also be accomplished by application of growth hormone releasing peptides (GRP's), some of which have been previously described (C.f. C. Y. Bowers et al., *Endocribology* 114, 1537 (1984), F. A. Momany et. al., *Endocrinology* 114, 1531 (1984) and C. Y. Bowers, *7th International Congress of Endocrinology Abstracts*, 464 (1984)).

Antibodies to the endogenous growth hormone release inhibitor, somatostatin (SRIF) are also used to elevate GH levels. In the last case, growth hormone levels are elevated by removing the endogenous GH-release inhibitor (SRIF) before it reaches the pituitary, where it inhibits the release of GH (c.f. W. B. Wehrenberg et al., *Endocribology* 115, 1218 (1984)).

Finally, it has been shown that some compounds such as morphine (c.f. C. Rivier et al., *Endocrinology* 100, 238 (1977)) and other alkaloids (c.f. C. Y. Bowers, *Endocrinology* 117, 1441 (1985)) and DAla$^2$, DLeu$^5$-enkephalinamide (c.f. E. L. Lien et al., *FEBS Letters* 88, 208 (1978)) also release growth hormone by acting on the hypothalamus.

OBJECTS OF THE INVENTION

It is an object of the present invention to provide novel growth hormone releasing compounds which are capable of promoting the release and elevation of growth hormone levels in the blood of animals.

It is another object of the present invention to provide methods for promoting the release and/or elevation of growth hormone levels in the blood of animals.

These and other objects of the present invention will become apparent from inspection of the following description and claims.

STATEMENT OF THE INVENTION

In accordance with the present invention, we have discovered several novel polypeptide compounds which promote the release of growth hormone in animals. The novel polypeptide compounds of the present invention have from seven up to eleven amino acid residues each. The preparation, characterization and administration of these novel growth hormone releasing compounds will now be described in greater detail.

DETAILED DESCRIPTION OF THE INVENTION

The present invention is based on the discovery of several short chain (i.e., seven up to eleven amino acid residues) polypeptides which promote the release and elevation of growth hormone level in the blood of animals. The polypeptides contemplated to be within the scope of the present invention are defined by the following generic structure:

X-AA1-AA2-AA3-AA4-Trp-AA6-AA7-Z, wherein X is selected from the group consisting of H, DOPA, Lys, Phe, Tyr, Cys, Tyr-DAla-Phe-Gly, Tyr-DAla-Gly-Phe and Tyr-Ala-Gly-Thr;

AA1 is selected from the group consisting of all naturally occurring L-amino acids, as well as Met(0), DOPA and Abu;

AA2 is selected from the group consisting of His and 3(NMe)+His (i.e., wherein the imidazole ring is methylated at the 3-position);

AA3 is selected from the group consisting of DTrp, 5-fluoro-D or D/Ltrp: 6-fluoro-D or D/Ltrp (i.e., wherein the indole ring is fluorinated at the 5- or 6-position), (formyl)DTrp (i.e., DTrp which is formylated at the indole nitrogen), and *XTrp, wherein *XTrp is selected from the group consisting of the N-monomethylated DTrp isomers (i.e., (N$^\alpha$Me) DTrp and (indole NMe)DTrp);

AA4 is selected from the group consisting of Ala, Gly and Ser;

AA6 is selected from the group consisting of DPhe and (NMe)DPhe;

AA7 is selected from the group consisting of Arg, iLys and Orn; and

Z represents the C terminal end group of said polypeptide or the C terminal amino acid(s) plus end group, wherein Z is selected from the group consisting of —CONH$_2$, —COOH, —COOR, —CONHR, —CONR$_2$, —CH$_2$OH and —CH$_2$OR, wherein R is an alkyl group having 1-6 carbon atoms or an aromatic ring having up to 12 carbon atoms: and wherein Z is alternatively selected from the group consisting of —Gly—Z', —Met—Z', —Lys—Z', —Cys—Z' (note that when a Cys moiety is also present in the 1 position of the polypeptide (i.e., X or AA1 is Cys), the resulting peptide can exist in the linear form or in the cyclic form), —Gly—Tyr—Z', and —Ala—Tyr—Z', wherein Z' is selected from the group consisting of —CONH$_2$, —CONHR, —COOH, —COOR, —CONR$_2$, —CH$_2$OH, and —CH$_2$OR, wherein R is a defined above:

and organic or inorganic addition salts of any of said polypeptides:

Wherein the amino acid residue abbreviations used are in accordance with the standard peptide nomenclature:

| | |
|---|---|
| Gly = | Glycine |
| Tyr = | L-Tyrosine |
| Ile = | L-Isoleucine |
| Glu = | L-Glutamic Acid |
| Thr = | L-Threonine |

| | -continued |
|---|---|
| Phe = | L-Phenylalanine |
| Ala = | L-Alanine |
| Lys = | L-Lysine |
| Asp = | L-Aspartic Acid |
| Cys = | L-Cysteine |
| Arg = | L-Arginine |
| Gln = | L-Glutamine |
| Pro = | L-Proline |
| Leu = | L-Leucine |
| Met = | L-Methionine |
| Ser = | L-Serine |
| Asn = | L-Asparagine |
| His = | L-Histidine |
| Trp = | L-Tryptophan |
| Val = | L-Valine |
| DOPA = | 3,4-L-Dihydroxyphenylalanine |
| Met(O) = | L-Methionine sulfoxide |
| iLys = | $N^\epsilon$—Isopropyl-L-lysine |
| Abu = | alpha-L-Aminobutyric acid |
| Orn = | L-Ornithine |
| Pal = | 3-Pyridyl-L-alanine |
| Pgl = | L-Phenylglycine |
| (beta)Ala = | beta alanine (i.e., 3-aminopropanoic acid) |

All three letter amino acid abbreviations preceded by a "D" indicate the D-configuration of the amino acid residue.

The flexibility associated with the choice of basic, neutral or acidic amino acid residues for amino acid AA1 provides one with a great deal of control over the physiochemical properties of the desired peptide. Such flexibility provides important advantages for the formulation and delivery of the desired peptide to any given species. Additional flexibility can be imparted by the fact that other amino acids (e.g., AA2, AA3, AA4, AA6, AA7) can be varied, as well as the moieties R, X and Z, thereby providing added control over the physiochemical properties of the desired compound.

Preferred growth hormone releasing compound employed in the practice of the present invention are selected from the group consisting of:
Ala-His-DTrp-Ala-Trp-DPhe-Lys-Gly-Tyr-Z';
Ala-His-(formyl)DTrp-Ala-Trp-DPhe-Lys-Z'(DTrp is formylated at the indole nitrogen):
Ala-His-DTrp-Ser-Trp-DPhe-Lys-Z':
Cys-Ala-His-DTrp-Ala-Trp-DPhe-Lys-Cts-Z'(cyclic disulfide);
Cys-Ala-His-DTrp-Ala-Trp-DPhe-Lys-Cys-Z'(free dithiol);
DOPA-Ala-His-DTrp-Ala-Trp-DPhe-Lys-Z';
His-DTrp-Ala-Trp-DPhe-Lys-Ala-Tyr-Z';
Lys-Ala-His-DTrp-Ala-Trp-DPhe-Lys-Z';
Phe-Ala-His-DTrp-Ala-Trp-DPhe-Lys-Z';
Tyr-Ala-Gly-Thr-Ala-His-DTrp-Ala-Trp-Dphe-Lys-Z';
Tyr-Ala-His-DTrp-Ala-Trp-DPhe-Lys-Z';
Tyr-DAla-Phe-Gly-Ala-His-DTrp-Ala-Trp-DPhe-Lys-Z';
Tyr-DAla-Gly-Phe-Ala-His-DTrp-Ala-Trp-DPhe-Lys-Z';
Ala-His-DTrp-Ala-Trp-DPhe-iLys-Z';
Ala-His-Dtrp-Ala-Trp-(NMe)DPhe-Lys-Z';
Ala-His-*XTrp*-Ala-Trp-DPhe-Lys-Z'(*XTrp* is selected from the group consisting of 5-fluoro-D or D/LTrp: 6-fluoro-D or D/LTrp (i.e., wherein the indole ring is fluorinated at the 5- or 6-position), and the N-monomethylated DTrp isomers, i.e., ($N^\alpha$-Me)DTrp, and (indole NMe)DTrp);
AA1-His-DTrp-Ala-Trp-DPhe-Lys-Z';
wherein AA1 is selected from the group consisting of all naturally occurring L-amino acids, as well as Met(0), DOPA and Abu; and wherein Z' and R are as defined above; and organic or inorganic addition salts of any of said polypeptides.

These compounds are preferred because of their ease of synthesis, proven efficacy at promoting the increase in serum growth hormone levels, and their consequent appeal for commercial scale production and utilization. In addition, these compounds may be advantageous in having physiochemical properties which are desirable for the efficient delivery of such polypeptide compounds to a variety of animal species. Because of the flexibility made possible by the various substitutions at numerous positions of the invention polypeptide compounds, a wide range of delivery vehicles can be employed, by selecting the polar, neutral or non-polar nature of the N-terminal, C-terminal and center portions of these polypeptide compounds so as to be compatible with the desired method of delivery.

In a most preferred embodiment, growth hormone releasing peptides employed in the practice of the present invention are selected from the group consisting of:
DOPA-Ala-His-DTrp-Ala-Trp-DPhe-Lys-Z";
His-Dtrp-Ala-Trp-DPhe-Lys-Ala-Tyr-Z";
Lys-Ala-His-DTrp-Ala-Trp-DPhe-Lys-Z";
Tyr-Ala-His-DTrp-Ala-Trp-DPhe-Lys-Z";
Phe-Ala-His-DTrp-Ala-Trp-DPhe-Lys-Z";
Ala-His-DTrp-Ala-Trp-DPhe-iLys-Z";
Ala-His-DTrp-Ala-Trp-(NMe)DPhe-Lys-Z";
Ala-His-DTrp-Ala-Trp-DPhe-Lys (as the free carboxylate);
AA1-His-Dtrp-Ala-Trp-DPhe-Lys-Z";
wherein AA'is selected from the group consisting of all naturally occurring L-amino acids, as well as DOPA, Met(0) and Abu,
wherein Z" is —CONH$_2$, and
wherein organic or inorganic addition salts of any of said polypeptides.

These compounds are the presently most preferred because these shorter chain polypeptides are less expensive to synthesize, and these specific compounds have been shown to have a high level of potency at promoting the increase in serum growth hormone levels. In addition, these compounds have advantageous physiochemical properties which allow efficient transport of such polypeptides to the receptor site for promotion of GH release. Note that these compounds retain the flexibility to be altered at both the N-terminal end and the C-terminal end, in order to maximum the compatibility of the polypeptide compound with the species being treated and the delivery vehicle being employed.

The compounds of this invention may be used to enhance blood GH levels in animals; enhance milk production in cows; enhance body growth in animals such as mammals (e.g., humans, sheep, bovines, and swine), as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like.

The novel polypeptide compounds of this invention can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIO-BEADS SX-1 by Bio Rad Laboratories, Richmond, Calif. The preparation of the hydroxy-methyl resin is described by Bodansky et al., *Chem. Ind.* (London) 38, 1597 (1966). The BHA resin has been described by Pietta and Marshall, *Chem. Commn.*, 650 (1970) and is commercially available from Penninsula Laboratories, Inc., Belmont, Calif. or Beckman Instruments, Inc., Palo Alto, Calif., in the hydrochloric form thereof (BHA.HCl).

After the initial attachment, the alpha-amino protecting group can be removed by a choice of acidic reagents, including trifluoroacetic acit (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such as dicyclohexycarbodiimide (DCC) in solution, for example, in methylene chloride ($CH_2Cl_2$) or dimethylformamide (DMF) and mixtures thereof.

After the desired amino acid sequence has been completed, the desired peptide can be cleaved from the resin support by treatment with a reagent such as hydrogen fluoride (HF) which not only cleaves the peptide from the resin, but also cleaves most commonly used sidechain protecting groups. When a chloromethyl resin or hydroxymethyl resin is used, HF treatment results in the formation of the free peptide acid. When the BHA of p-Me-BHA resin is used, HF treatment results directly in free peptide amides.

The solid-phase procedure discussed above is well known in the art and has been described by Stewart and Young, *Solid Phase Peptide Synthesis*: (Freeman and Co., San Francisco, Calif., 1969).

Some of the well known solution methods which can be employed to synthesize the peptide moieties of the instant invention are set forth in Bodansky et al., *Peptide Synthesis*, 2nd Edition, John Wiley & Sons, New York, N.Y. 1976.

In accordance with another embodiment of the present invention, a method is provided for promoting release and/or elevation of growth hormone levels in the blood of an animal. Said method comprises administering to an animal an effective dose of at least one of the above-described polypeptides.

The compounds of this invention can be administered by oral, parenteral (intramuscular (i.m.), intraperitoneal (i.p.), intravenous (i.v.) or subcutaneous (s.c.) injection), nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is mixed with at least one inert carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsigying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

As previously disclosed in our copending applications Ser. No. 861,968 and Ser. No. 37,275, the novel compounds of the present invention are also useful when administered in combination with growth hormone releasing hormone (i.e., naturally occurring growth hormone releasing hormone, analogs and functional equivalents thereof), as well as in combination with growth hormone releasing peptides which act on the hypothalamus (rather than acting on the pituitary gland) and thyrotropin releasing hormone (TRH). Such combinations represent an especially preferred means to administer the growth hormone releasing peptides of the present invention. For further detail on the administration of combinations of growth hormone releasing peptides, those of skill in the art are referred to the above-cited application.

The amount of polypeptide or combination of polypeptides of the present invention administered will vary depending upon the particular animal treated, its age and sex, the desired therapeutic affect, the route of administration and which polypeptide or combination of polypeptides are employed. In all instances, however, a dosage effective to promote release and elevation of growth hormone level in the blood of the recipient animal is used. Ordinarily, this dosage level falls in the range of between about 0.1 μg up to 10 mg of total polypeptide per kg of body weight. In general, the administration of combinations of growth hormone releasing peptides will allow for lower doses of the individual growth hormone releasing compounds to be employed relative to the dosage levels required for individual growth hormone releasing compounds in order to obtain a similar response, due to the synergistic effect of the combination.

Also included within the scope of the present invention are compositions comprising, as an active ingredient, the organic and inorganic addition salts of the above described polypeptides optionally thereof, in association with a carrier, diluent, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e., alkaline earth metal salts) ammonium and protamine salts, zinc, iron, and the like with counterions such as the chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including the sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The invention will now be described in greater detail be reference to the following non-limiting examples.

EXAMPLE 1

Synthesis of the Growth Hormone Releasing Peptides

Paramethyl benzhydrylamine hydrochloride (p-MeBHA.HCl) resin is placed in a reaction vessel on a commercially available automated peptide synthesizer. The resin is substituted with free amine up to a loading of about 5 mmoles per gram. The compounds are prepared by coupling individual amino acids starting at the carboxy terminus of the peptide sequence using an appropriate activating agent, such as N,N'-dicyclohexylcarbodiimide (DCC). The alpha amine of individual amino acids are protected, for example, as the t-butyloxycarbonyl derivative (t-Boc) and the reactive side chain functionalities are protected as outlined in Table 1.

TABLE 1

| Side Chain Protecting Groups Suitable for Solid Phase Peptide Synthesis | |
|---|---|
| Arginine: | $N^g$—Tosyl |
| Aspartic Acid: | O—Benzyl |
| Cysteine: | S—para-Methylbenzyl |
| Glutamic Acid: | O—Benzyl |
| Histidine: | $N^{im}$—Tosyl |
| Lysine: | $N^\epsilon$—2,4-Dichlorobenzyloxycarbonyl |
| Methionine: | S—Sulfoxide |
| Serine: | O—Benzyl |
| Threonine: | O—Benzyl |
| Tryptophan: | $N^{in}$—Formyl |
| Tyrosine: | O—2,6-Dichlorobenzyl |

Prior to incorporation of the initial amino acid, the resin is agitated three times (about one minute each) with dichloromethane ($CH_2Cl_2$; about 10 ml/gm of resin), neutralized with three agitations (about two minutes each) of N,N-diisopropylethylamine (DIEA) in dichloromethane (10:90; about 10 ml/gm of resin) and agitated three times (about one minute each) with dichloromethane (about 10 ml/gm of resin). The initial and each of the subsequent amino acids are coupled to the resin using a preformed symmetrical anhydride using about 3.0 times the total amount of the binding capacity of the resin of a suitably protected amino acid and about 1.5 times the total amount of the binding capacity of the resin of DCC in an appropriate amount of dichloromethane. For amino acids with a low dichloromethane solubility, N,N-dimethylformamide (DMF) is added to achieve a homogenous solution. Generally, the symmetrical anhydride is prepared up to 30 minutes prior to introduction into the reaction vessel at room temperature or below. The dicyclohexylurea that forms upon preparation of the symmetrical anhydride is removed via gravity filtration of the solution into the reaction vessel. Progress of the coupling of the amino acid to the resin is commly monitored via a color test using a reagent such as ninhydrin (which reacts with primary and secondary amines. Upon complete coupling of the protected amino acid to the resin (>99%), the alpha amine protecting group is removed by a series of acidic reagents. A commonly used reagent consists of a solution of trifluoroacetic acid (TFA), and anisole in dichloromethane (45:2:53). The complete procedure for incorporation of each individual amino acid residue onto the resin is outlined in Table 2.

TABLE 2

Procedure for Incorporation of Individual Amino Acids onto a Resin

| | Reagent | Agitations | Time/Agitation |
|---|---|---|---|
| 1. | Dichloromethane | 3 | 1 min. |
| 2. | TFA, Anisole, Dichloromethane (45:2:53) | 1 | 2 min. |
| 3. | TFA, Anisole, Dichloromethane (45:2:53) | 1 | 20 min. |
| 4. | Dichloromethane | 3 | 1 min. |
| 5. | DIEA. Dichloromethane (10:90) | 3 | 2 min. |
| 6. | Dichloromethane | 3 | 1 min. |
| 7. | Preformed symmetrical anhydride | 1 | 15-120 min.* |
| 8. | Dichloromethane | 3 | 1 min. |
| 9. | iso-Propanol | 3 | 1 min. |
| 10. | Dichloromethane | 3 | 1 min. |
| 11. | Monitor progress of the coupling reaction** | | |
| 12. | Repeat Steps 1-12 for each individual amino acid | | |

*Coupling time depends upon the individual amino acid.
**The extent of coupling can be generally monitored by a color test. If the couplinq is incomplete, the same amino acid can be recoupled by repeating Steps 7-11. If the coupling is complete the next amino acid can be coupled.

EXAMPLE 2

In Vivo GH Release in Rats

Immature female Sprague-Dawley rats were obtained from the Charles River Laboratories (Wilmington, MA). After arrival they were housed at 25° C. with a 14:10 hr light:dark cycle. Water and Puring rat chow were available ad libitum. Pups were kept with their mothers until 21 days of age.

Normal saline with 0.1% gelatin was the vehicle for intravenous (i.v.) injections of the peptides. In some experiments in which the peptides were very insoluble, DMSO was used to dissolve the compounds, with dilutions then being made to the specified concentration with normal saline with 0.1% gelatin (compounds for which DMSO was needed to effect solution are so noted in the Tables). The unanesthetized rats, weighing 55-65 grams, were injected i.v. with the quantity of growth hormone releasing compounds indicated in Tables 3-4. Injection was made as a 0.2 ml solution via the tail vein. All animals were sacrificed by guillotine 10 min after the final test injection (see Table 3) or 30 minutes after the final test injection (see Table 4). Trunk blood for the determination of blood GH levels was collected following decapitation. After allowing the blood to clot, it was centrifuged and the serum was separated from the clot. Serum was kept frozen until the day of sampling for radioimmunoassay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:

(a) buffer, (b) "cold" (i.e., non-radioactive) standard or unknown serum sample to be analyzed, (c) radio-iodinated growth hormone antigen, and (d) growth hormone antiserum. Reagent addition is generally carried out so that there is achieved a final RIA tube dilution of about 1:30,000 (antiserum to total liquid volume; vol:vol).

The mixed reagents are then typically incubated at room temperature (about 25° C.) for about 24 hours prior to addition of a second antibody (e.g., goat or rabbit anti-monkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts versus growth hormone (GH) level. GH levels of unknowns are then determined by reference to the standard curve.

Serum GH was measured by RIA with reagents provided by the National Hormone and Pituitary Program.

Serum levels in tables 3 and 4 are recorded in ng/ml in terms of the rat GH standard of 0.61 International Units/mg (IU/mg). Data is recorded as the mean +/− standard error of the mean (SEM). Statistical analysis was performed with Student's t-test. In Tables 3 and 4 the results shown are the average of studies with six rats.

TABLE 3

In Vivo GH Release (ng/ml) Promoted by Growth Hormone Releasing Compounds
(Animals Sacrificed 10 Minutes After Final Injection

| Number | Column A Growth Hormone Releasing Compounds | Total Dose (μg) | Control GH ng/ml | GH Released by Compound in Column A ng/ml |
|---|---|---|---|---|
| 8937 | (beta)Ala—His—DTrp—Ala—Trp—DPhe—Lys—NH2 | 10 | 10 ± 1.4 | 32 ± 4 |
| 8588 | Ala—His—DPal—Ala—Trp—DPhe—Lys—NH2 | 100 | 8 ± 8 | 19 ± 5 |
| 8323 | Ala—His—DTrp—Ala—Pal—DPhe—Lys—NH2 | 100 | 3 ± 0.5 | 18 ± 1 |
| 9308 | Ala—Cys—DTrp—Ala—Trp—DPhe—Lys—Cys—NH2* | 10 | 14 ± 2.0 | 10 ± 1 |
| 9887 | Ala—His—DTrp—Ala—Trp—DPgl—Lys—NH2* | 10 | 13 ± 1.0 | 11 ± 1 |
| 9090 | Ala—His—DTrp—DLys—Trp—DPhe—Lys—NH2* | 10 | 7 ± 2.0 | 14 ± 3 |
| 10265 | Ala—His—DArg—Ala—Trp—DPhe—Lys—NH2* | 10 | 13 ± 2 | 14 ± 2 |
| 10351 | DDopa—Ala—His—DTrp—Ala—Trp—DPhe—Lys—NH2* | 10 | 12 ± 2 | 13 ± 2 |
| 8758 | Cys—Ala—His—DTrp—Ala—Trp—DPhe—Lys—Cys—NH2** | 10 | 8.0 ± 2.0 | 37 ± 8 |
| 8758 | Cys—Ala—His—DTrp—Ala—Trp—DPhe—Lys—Cys—NH2** | 10 | 14.0 ± 2.0 | 26 ± 9 |
| 8114 | Ala—His—DTrp—Ala—Trp—DPhe—Lys—NH2 | 10 | 3.0 ± 0.5 | 93 ± 30 |
| 8114 | Ala—His—DTrp—Ala—Trp—DPhe—Lys—NH2 | 10 | 17.0 ± 3.0 | 129 ± 46 |
| 8114 | Ala—His—DTrp—Ala—Trp—DPhe—Lys—NH2 | 10 | 10.0 ± 1.4 | 52 ± 8 |
| 8114 | Ala—His—DTrp—Ala—Trp—DPhe—Lys—NH2 | 10 | 7.0 ± 2.0 | 54 ± 7 |
| 8114 | Ala—His—DTrp—Ala—Trp—DPhe—Lys—NH2 | 10 | 12.0 ± 1.0 | 72 ± 9 |
| 8114 | Ala—His—DTrp—Ala—Trp—DPhe—Lys—NH2 | 10 | 14.0 ± 2.0 | 119 ± 28 |
| 8114 | Ala—His—DTrp—Ala—Trp—DPhe—Lys—NH2 | 10 | 7.3 ± 2.0 | 55 ± 13 |
| 8114 | Ala—His—DTrp—Ala—Trp—DPhe—Lys—NH2 | 10 | 2.2 ± 0.6 | 152 ± 40 |
| 8114 | Ala—His—DTrp—Ala—Trp—DPhe—Lys—NH2 | 10 | 14.0 ± 1.0 | 132 ± 36 |
| 8114 | Ala—His—DTrp—Ala—Trp—DPhe—Lys—NH2 | 10 | 9.0 ± 4.0 | 105 ± 37 |
| 8114 | Ala—His—DTrp—Ala—Trp—DPhe—Lys—NH2 | 10 | 7.0 ± 0.6 | 117 ± 36 |
| 8114 | Ala—His—DTrp—Ala—Trp—DPhe—Lys—NH2 | 10 | 2.0 ± 0.2 | 115 ± 50 |
| 8114 | Ala—His—DTrp—Ala—Trp—DPhe—Lys—NH2 | 10 | 6.0 ± 0.7 | 169 ± 60 |
| 8114 | Ala—His—DTrp—Ala—Trp—DPhe—Lys—NH2 | 10 | 9.0 ± 1.0 | 210 ± 42 |
| 8114 | Ala—His—DTrp—Ala—Trp—DPhe—Lys—NH2 | 10 | 18.0 ± 3.0 | 255 ± 73 |
| 8114 | Ala—His—DTrp—Ala—Trp—DPhe—Lys—NH2 | 10 | 10.0 ± 1.0 | 315 ± 65 |

TABLE 3-continued

In Vivo GH Release (ng/ml) Promoted by Growth Hormone Releasing Compounds.
(Animals Sacrificed 10 Minutes After Final Injection

| Number | Column A Growth Hormone Releasing Compounds | Total Dose (µg) | Control GH ng/ml | GH Released by Compound in Column A ng/ml |
|---|---|---|---|---|
| 8114 | Ala—His—DTrp—Ala—Trp—DPhe—Lys—NH2 | 10 | 30.0 ± 1.0 | 114 ± 20 |
| 8866 | Tyr—Ala—Gly—Thr—Ala—His—DTrp—Ala—Trp—DPhe—Lys—NH2 | 10 | 8.0 ± 2.0 | 177 ± 38 |
| 8866 | Tyr—Ala—Gly—Thr—Ala—His—DTrp—Ala—Trp—DPhe—Lys—NH2 | 30 | 8.0 ± 2.0 | 144 ± 38 |
| 8866 | Tyr—Ala—Gly—Thr—Ala—His—DTrp—Ala—Trp—DPhe—Lys—NH2 | 10 | 14.0 ± 1.0 | 292 ± 42 |
| 9106 | Tyr—DAla—Phe—Gly—Ala—His—DTrp—Ala—Trp—DPhe—Lys—NH2 | 100 | 14.0 ± 1.0 | 116 ± 42 |
| 9216 | Tyr—DAla—Gly—Phe—Ala—His—DTrp—Ala—Trp—DPhe—Lys—NH2 | 30 | 12.0 ± 1.0 | 46 ± 12 |
| 9216 | Tyr—DAla—Gly—Phe—Ala—His—DTrp—Ala—Trp—DPhe—Lys—NH2 | 100 | 14.0 ± 1.0 | 196 ± 43 |
| 8938 | His—DTrp—Ala—Trp—DPhe—Lys—NH2 | 10 | 3.0 ± 0.5 | 70 ± 29 |
| 9036 | His—DTrp—Ala—Trp—DPhe—Lys—Ala—Tyr—NH2 | 10 | 10.0 ± 1.0 | 52 ± 7 |
| 9020 | Abu—His—DTrp—Ala—Trp—DPhe—Lys—NH2 | 10 | 18.0 ± 11.0 | 85 ± 24 |
| 9868 | DOPA—Ala—His—DTrp—Ala—Trp—DPhe—Lys—NH2 | 10 | 13.0 ± 1.0 | 123 ± 30 |
| 10276 | Leu—His—DTrp—Ala—Trp—DPhe—Lys—NH2 | 10 | 13.0 ± 2 | 190 ± 58 |
| 10276 | Leu—His—DTrp—Ala—Trp—DPhe—Lys—NH2 | 10 | 13.0 ± 1.0 | 74 ± 25 |
| 10321 | Val—His—DTrp—Ala—Trp—DPhe—Lys—NH2 | 10 | 13.0 ± 2 | 137 ± 28 |
| 10337 | Phe—Ala—His—DTrp—Ala—Trp—DPhe—Lys—NH2 | 10 | 12.0 ± 2.0 | 68 ± 11 |
| 10337 | Phe—Ala—His—DTrp—Ala—Trp—DPhe—Lys—NH2 | 10 | 14.0 ± 2.0 | 132 ± 45 |
| 10391 | Ala—His—DTrp—Ala—DPhe—Lys—Gly—Tyr—NH2 (a) | 10 | 12.0 ± 2.0 | 36 ± 6 |
| 10391 | Ala—His—DTrp—Ala—DPhe—Lys—Gly—Tyr—NH2 (a) | 10 | 14.0 ± 2.0 | 155 ± 59 |
| 10321 | Val—His—DTrp—Ala—Trp—DPhe—Lys—NH2 | 1 | 5.0 ± 0.4 | 11 ± 2 |
| 10321 | Val—His—DTrp—Ala—Trp—DPhe—Lys—NH2 | 3 | 5.0 ± 0.4 | 129 ± 13 |
| 10321 | Val—His—DTrp—Ala—Trp—DPhe—Lys—NH2 | 10 | 5.0 ± 0.4 | 68 ± 29 |
| 10855 | Ala—His—(formyl)DTrp—Ala—Trp—DPhe—Lys—NH2 | 10 | 6.0 ± 1.0 | 19 ± 6 |
| 10814 | Dopa—His—DTrp—Ala—Trp—DPhe—Lys—NH2 | 3 | 6.0 ± 1.0 | 67 ± 17 |
| 10814 | Dopa—His—DTrp—Ala—Trp—DPhe—Lys—NH2 | 10 | 6.0 ± 1.0 | 76 ± 20 |
| 10957 | Trp—His—DTrp—Ala—Trp—DPhe—Lys—NH2 (b) | 10 | 7.0 ± 1.0 | 127 ± 23 |
| 10957 | Trp—His—DTrp—Ala—Trp—DPhe—Lys—NH2 (b) | 30 | 7.0 ± 1.0 | 268 ± 58 |
| 10873 | Met—His—DTrp—Ala—Trp—DPhe—Lys—NH2 (b) | 10 | 7.0 ± 1.0 | 65 ± 18 |
| 10873 | Met—His—DTrp—Ala—Trp—DPhe—Lys—NH2 (b) | 30 | 7.0 ± 1.0 | 161 ± 47 |
| 10973 | Ala—His—DTrp—Ser—Trp—DPhe—Lys—NH2 (b) | 10 | 7.0 ± 0.5 | 30 ± 7 |
| 11009 | Lys—His—DTrp—Ala—Trp—DPhe—Lys—NH2 (b) | 3 | 5.0 ± 0.4 | 57 ± 9 |
| 11009 | Lys—His—DTrp—Ala—Trp—DPhe—Lys—NH2 (b) | 10 | 5.0 ± 0.4 | 217 ± 64 |
| 11012 | Asp—His—DTrp—Ala—Trp—DPhe—Lys—NH2 | 10 | 7.0 ± 0.5 | 128 ± 48 |
| 11012 | Asp—His—DTrp—Ala—Trp—DPhe—Lys—NH2 | 10 | 12.0 ± 0.5 | 107 ± 26 |
| 18988 | Met(O)—His—DTrp—Ala—Trp—DPhe—Lys—NH2 | 10 | 14.0 ± 0.5 | 65 ± 17 |
| 18988 | Met(O)—His'DTrp—Ala—Trp—DPhe—Lys—NH2 | 10 | 5.0 ± 0.4 | 90 ± 25 |
| 11553 | Tyr—Ala—His—DTrp—Ala—Trp—DPhe—Lys—NH2 | 10 | 6.5 ± 0.5 | 170 ± 38 |
| 11561 | Lys—His—DTrp—Ala—Trp—DPhe—Asp—NH2 | 3 | 8.0 ± 1.0 | 9 ± 1 |
| 11561 | Lys—His—DTrp—Ala—Trp—DPhe—Asp—NH2 | 10 | 8.0 ± 1.0 | 11 ± 1 |

TABLE 3-continued

In Vivo GH Release (ng/ml) Promoted by Growth Hormone Releasing Compounds
(Animals Sacrificed 10 Minutes After Final Injection

| Number | Column A Growth Hormone Releasing Compounds | Total Dose (μg) | Control GH ng/ml | GH Released by Compound in Column A ng/ml |
|---|---|---|---|---|
| 11562 | Arg—His—DTrp—Ala—Trp—DPhe—Lys—NH$_2$ | 3 | 8.0 ± 1.0 | 50 ± 17 |
| 11562 | Arg—His—DTrp—Ala—Trp—DPhe—Lys—NH$_2$ | 10 | 8.0 ± 1.0 | 87 ± 27 |
| 11603 | Lys—Ala—His—DTrp—Ala—Trp—DPhe—Lys—NH$_2$ | 3 | 16.0 ± 3.0 | 41 ± 5 |
| 11603 | Lys—Ala—His—DTrp—Ala—Trp—DPhe—Lys—NH$_2$ | 10 | 16.0 ± 3.0 | 82 ± 19 |
| 11603 | Lys—Ala—His—DTrp—Ala—Trp—DPhe—Lys—NH$_2$ | 30 | 16.0 ± 3.0 | 135 ± 38 |
| 11839 | Ala—His—DTrp—Ala—Trp—DPhe—iLys—NH$_2$ | 3 | 12.0 ± 3.0 | 30 ± 7 |
| 11839 | Ala—His—DTrp—Ala—Trp—DPhe—iLys—NH$_2$ | 10 | 12.0 ± 3.0 | 59 ± 18 |
| 11839 | Ala—His—DTrp—Ala—Trp—DPhe—iLys—NH$_2$ | 30 | 12.0 ± 3.0 | 246 ± 63 |
| 12392 | His—His—DTrp—Ala—Trp—DPhe—Lys—NH$_2$ | 10 | 10.0 ± 0 | 479 ± 64 |

*compounds so designated are structurally similar to the growth hormone releasing compounds according to the invention, but do not display the ability to promote the release of growth hormone promoted by invention compounds.
**contains cyclic disulfide bridge between Cys groups
(a) Compound initially dissolved in 10 mM acetic acid
(b) Invention compound initially dissolved in DMSO, then diluted as described in the text.

TABLE 4

In Vivo GH Release (ng/ml) Promoted by Growth Hormone Releasing Compounds
(Animals Sacrificed 30 Minutes After Final Injection

| Number | Column A Growth Hormone Releasing Compounds | Total Dose (ng) | Control GH ng/ml | GH Released by Compound in Column A ng/ml |
|---|---|---|---|---|
| 8114 | Ala—His—DTrp—Ala—Trp—DPhe—Lys—NH$_2$ | 20 | NA* | 69 ± 6 |
| 8114 | Ala—His—DTrp—Ala—Trp—DPhe—Lys—NH$_2$ | 20 | 5 ± 2 | 46 ± 7 |
| 8114 | Ala—His—DTrp—Ala—Trp—DPhe—Lys—NH$_2$ | 20 | 8 ± 3 | 94 ± 27 |
| 11603 | Lys—Ala—His—DTrp—Ala—Trp—DPhe—Lys—NH$_2$ | 20 | NA | 105 ± 14 |
| 11009 | Lys—His—DTrp—Ala—Trp—DPhe—Lys—NH$_2$ | 20 | NA | 131 ± 26 |
| 11009 | Lys—His—DTrp—Ala—Trp—DPhe—Lys—NH$_2$ | 20 | 5 ± 2 | 35 ± 9 |
| 10337 | Phe—Ala—His—DTrp—Ala—Trp—DPhe—Lys—NH$_2$ | 20 | NA | 102 ± 9 |
| 10814 | DOPA—His—DTrp—Ala—Trp—DPhe—Lys—NH$_2$ | 20 | NA | 105 ± 10 |
| 10765 | DOPA—Ala—His—DTrp—Ala—Trp—DPhe—Lys—NH$_2$ | 20 | NA | 30 ± 7 |
| 10276 | Leu—His—DTrp—Ala—Trp—DPhe—Lys—NH$_2$ | 20 | NA | 98 ± 29 |
| 10321 | Val—His—DTrp—Ala—Trp—DPhe—Lys—NH$_2$ | 20 | NA | 156 ± 39 |
| 10321 | Val—His—DTrp—Ala—Trp—DPhe—Lys—NH$_2$ | 20 | 8 ± 3 | 93 ± 25 |
| 10021 | Asp—His—DTrp—Ala—Trp—DPhe—Lys—NH$_2$ | 20 | NA | 135 ± 17 |
| 10957 | Trp—His—DTrp—Ala—Trp—DPhe—Lys—NH$_2$ | 20 | NA | 134 ± 38 |
| 10957 | Trp—His—DTrp—Ala—Trp—DPhe—Lys—NH$_2$ | 20 | 5 ± 2 | 66 ± 16 |
| 10873 | Met—His—DTrp—Ala—Trp—DPhe—Lys—NH$_2$ | 20 | NA* | 159 ± 4 |
| 10873 | Met—His—DTrp—Ala—Trp—DPhe—Lys—NH$_2$ | 20 | 5 ± 2 | 46 ± 15 |
| 10873 | Met—His—DTrp—Ala—Trp—DPhe—Lys—NH$_2$ | 20 | 8 ± 3 | 95 ± 20 |
| 9020 | Abu—His—DTrp—Ala—Trp—DPhe—Lys—NH$_2$ | 20 | NA | 72 ± 8 |
| 0933 | Ala—His—DTrp—Ala—Trp—DPhe—Lys—NH$_2$ | 20 | NA | 86 ± 19 |
| 10391 | Ala—His—DTrp—Ala—Trp—DPhe— | 20 | 6 ± 1 | 47 ± 8 |

TABLE 4-continued

In Vivo GH Release (ng/ml) Promoted by Growth Hormone Releasing Compounds
(Animals Sacrificed 30 Minutes After Final Injection

| Number | Column A Growth Hormone Releasing Compounds | Total Dose (ng) | Control GH ng/ml | GH Released by Compound in Column A ng/ml |
|---|---|---|---|---|
| 8758 | Lys—Gly—Tyr—NH$_2$ Cys—Ala—His—DTrp—Ala—Trp—DPhe—Lys—Cys—NH$_2$ (cyclic disulfide) | 20 | 6 ± 1 | 52 ± 7 |
| 8866 | Tyr—Ala—Gly—Thr—Ala—His—DTrp—Ala—Trp—DPhe—Lys—NH$_2$ | 20 | 6 ± 1 | 32 ± 8 |
| 11553 | Tyr—Ala—His—DTrp—Ala—Trp—DPhe—Lys—NH$_2$ | 20 | 6 ± 1 | 59 ± 12 |
| 11012 | Asp—His—DTrp—Ala—Trp—DPhe—Lys—NH$_2$ | 20 | 5 ± 2 | 74 ± 15 |
| 12392 | His—His—DTrp—Ala—Trp—DPhe—Lys—NH$_2$ | 20 | 5 ± 2 | 100 ± 16 |

*NA = Not Available in Tables 3 and 4, compounds of the invention are shown to promote the release and elevation of growth hormone levels in the blood of rats to which such compounds have been administered. These results are surprising in view of the lack of growth hormone releasing activity displayed by several strikingly similar compounds which are also included in Table 3.

Data in Table 4 further demonstrate the prolonged period (30 minutes versus 10 minutes for data in Table 3) over which compounds of the invention are effective at promoting the release and elevation of growth hormone levels.

EXAMPLE 3

In Vivo Growth Hormone Release Study - Lambs

Female lambs (20–28 kg) were housed in individual cages in a constant temperature room at 24° C. with 12h—12h light-dark cycle. The lambs were fed a diet containing grade 2 corn, soybean meal, orchard grass hay, molasses and premix.

Various doses of the compound Ala-His-DTrp-Ala-Trp-Drphe-Lys-NH$_2$ (Compound #8114) were dissolved in 200 µl of 10mM acetic acid and brought to 5 ml with phosphate buffered saline (PBS). Lambs were catheterized via the jugular vein. Intravenous infusions were performed by using a multichannel infusion pump (Model 600-200, Harvard Apparatus Co., Inc., Dover, Mass.) preset at a flow rate of 1.36 ml/min. Sampling of blood was performed every 20 minutes starting 1 hour prior to treatment and continuing until 1 hour after treatment. Additional samples were taken at −10 min., +5 min and +10 min. Blood samples were drawn and deposited into EDTA-treated tubes for plasma preparation. EDTA treated plasma was analyzed for GH using a standard double antibody RIA, according to the following procedure:

PROCEDURE FOR LAMB GROWTH HORMONE RADIOIMMUNMOASSAY

REAGENTS

1. Phosphosaline Buffer (0.15 M NaCl −0.012 M Phosphate) (PSB):
Add 5.14 gm NaH$_2$PO$_4$.H$_2$O (monobasic) and 26.6 gm sodium chloride to 2.95 liters distilled water.
Add 2.0 M sodium hydroxide dropwise to bring pH to 7.5.
Add 3 ml merthiolate as preservative.
Bring toltal volume to 3.0 liters.
Store at 4° C..
2. Phosphosaline Buffer With 1% Bovine Serum Albumin (PBSA):
Dilute commercially available 30% solution of bovine serum albumin (BSA) thirtyfold with phosphosaline buffer (PSB).
Store at 4° C. and use without further dilution.
3. Ovine Growth Hormone Antiserum (rabbit):
Stored frozed at 1:10 dilution (as obtained).
Working dilution is 1:20,000. Prepare only enough dilution to last one week. Store at 4° C.. 4. Ovine Growth Hormone:
Prepare and store frozen in vials (2.5 µg/0.5 ml PBSA/vial). 5. Radioiodinated Ovine Growth Hormone (Approximately 10,000 cpm/100 µl). 6. Goat Anti-Rabbit Gamma Globulin (suggested sources, Antibodies, Inc., Cambridge Medical Diagnostics, Inc.) Stored frozen in 1 ml aliquots. 7. 6% PEG in PSB:
Weight 6.0 gm Polyethylene Glycol 6000.
Dilute to 100 ml in PSB (see 1).
Store at 4° C. 8. 0.5 M EDTA:
Weight 1.9 gm (Ethylenedinitrilo)-tetraacetic Acid Tetrasodium Salt.
Dilute to 100 ml in PSB (see 1).
Adjust pH to 7.5 with NaOH.
Store at 4° C.. 9. Normal Rabbit Serum:
Store frozen in 1.0 ml aliquots. 10. Normal Rabbit Serum:EDTA (1:400) (NRS:EDTA):
Dilute 0.25 ml NRS to 100 ml with 0.05 M EDTA (see 8);
Store at 4° C..

Assay Procedure (for 250 Tubes)

Day 1

1. Label 12×75 mm glass tubes as follows:
Tubes 1-2 (to be used to measure nonspecific binding NSB).
Tubes 3-4 (to be used to measure maximun binding B$_o$).
Tubes 5-6 (to be used to measure total counts).
Tubes 7-18 (to be used for standards A-F).
Starting with tubes 19, two tubes are consecutively numbered for each control or sample.
2. Add 4.5 ml PBSA to 2.5 µg/0.5 ml stock ovine growth hormone. (The concentration is now 500 ng/ml) continue to dilute standards as follows:

A - 0.25 ng/100 μl → dilute D 1/10
    (100 μl + 900 μl PBSA)
B - 0.5 ng/100 μl → dilute E 1/10
    (100 μl + 900 μl PBSA)
C - 1 ng/100 μl → dilute F 1/10
    (100 μl + 900 μl PBSA)
D - 2.5 ng/100 μl → dilute stock 1/20
    (50 μl + 950 μl PBSA)
E - 5 ng/100 μl → dilute stock 1/10
    (100 μl + 900 μl PBSA)
F - 10 ng/100 μl → dilute stock 1/5
    (200 μl + 800 μl PBSA)

3. Dilute ovine growth hormone antiserum (1:10 dilution) to 1:20,000 (25 μl antiserum +49.98 ml 1:400 NRS:EDTA). 4. Add 200 μl NRS:EDTA +500 μl PBSA to tubes 1 and 2. (to determine NSB). 5. Add 500 μl PBSA to tubes 3 and 4. (to determine $B_o$). 6. Add 100 μl of Standards A through F, controls or samples as follows:

| Tube No. | Standards, Controls or Samples |
|---|---|
| 7.8 | A |
| 9,10 | B |
| 11,12 | C |
| 13,14 | D |
| 15,16 | E |
| 17,18 | F |
| Sample | Unknown |

7. Add 400 μl PBSA to standards A-F and all samples. 8. Add 200 μl of diluted ovine growth hormone antiserum to all tubes except NSB (1 and 2) and total counts (5 and 6). 9. Vortex tubes, cover tubes and incubate at 40° C. for 20 hours.

Day 2

10. Add 100 μl of radioiodinated ovine growth hormone to all tubes. (Approximately 10,000 cpm/100 μl.) Vortex tubes and incubate at 4° C. for 20 hours.

Day 3

11. Dilute goat anit-rabbits gamma globulin to 1:10 or as stated on container with PBSA.

Add 200 μl of diluted goat anti-rabbit gamma globulin to all tubes (excepts tubes 5 and 6). Vortex tubes and incubate at room temperature for 15 minutes. 12. Add 1 ml 6% PEG in PSB to all tubes (except tubes 5 and 6). Vortex and centrifuge at 1500-1600 g for 25 minutes. 13. Measure precipitate for radioactivity counts using an LKB model 1275 gamma-scintillation counter.

Iodination grade ovine GH was obtained from the National Pituitary Center, and was used for iodination (Chloramine T method) and standard. The anti-ovine GH serum was also obtained from the National Pituitary Center. The results are presented in Table 5. The amount of growth hormone released is expressed as the maximum height of the growth hormone peak and the area under the growth hormone peak measured for one hour after the administration of Compound #8114.

TABLE 5

Effects of Compound #8114 on Plasma Growth Hormone Concentrations in Lambs

| Treatment | -GH Area Under Curve, ng-min/mL; (GH Maximum Peak Height, ng/ml)- Dose* | | |
|---|---|---|---|
|  | 1 μg/kg | 10 μg/kg | 30 μg/kg |
| Phosphate buffered saline (control) | 40 (3) | 73 (3) | 36 (2) |
| Compound #8114 | 67 (2) | 228 (7) | 1.086 (38) |

*Dose is the amount of the trifluoroacetic acid salt(s) of Compound #8114 administered. The actual percent peptide content of Compound #8114 administered can be determined by such well known procedures as elemental analysis or amino acid analysis.

In Table 5, compound #8114 is shown to promote the release and elevation of growth hormone levels in the blood of lambs to which the compound has been administered. The increase in blood growth hormone levels is also shown to be related to the dosage of Compound #8114.

EXAMPLE 4

In Vivo Growth Hormone Release Study -Beef Calves

Female beef calves (151-191 kg) were housed in individual cages in a constant temperature room at 24° C. with 12h—12h light-dark cycle. The beef calves were fed a diet containing cracked corn, corn silage, soybean meal, alfalfa hay, molasses and premix.

Various doses of the compound Ala-His-DTrp-Ala-Trp-DPhe-Lys-$NH_2$ (Compound #8114) were dissolved in 200 μl of 10 mM acetic and brought to 5 ml with phosphate buffered saline (PBS). The calves were catheterized via the jugular vein. Intravenous infusions were performed by using a multichannel infusion pump (Model 600-900, Harvard Apparatus Co., Inc., Dover, Mass.) preset at a flow rate of 1.36 ml/min. Sampling of blood was performed every 20 minutes starting one hour prior to treatment and continuing until three hours after treatment. Additional samples were taken at −10 min., +5 min., and +10 min. Blood samples were drawn and deposited into EDTA-treated tubes for plasma preparation. EDTA treated plasma was analyzed for GH using a standard double antibody RIA in accordance with the procedure set forth above. Iodination grade bovine growth hormone (bGH) was obtained from the National Pituitary Center, and was used for iodination and standard. The anti-bGH Serum was also obtained from the National Pituitary Center.

Results are presented in Table 6. The amount of growth hormone released is expressed as the maximum height of the growth hormone peak and the area under the growth hormone peak measured for these hours after the administration of #8114.

TABLE 6

Effects of Compound #8114 on Plasma Growth Hormone Concentrations in Beef Cattle

| Treatment | -GH Area Under Curve, ng-min/ml; (GH Maximum Peak Height, ng/ml)- Dose* | | |
|---|---|---|---|
|  | 1 μg/kg | 10 μg/kg | 30 μg/kg |
| Phosphate buffered saline | 412 (12) | 472 (11) | 703 (20) |
| Compound #8114 | 897 (16) | 2300 (66) | 4811 (99) |

*Dose is the amount of the trifluoroacetic acid salt(s) of Compound #8114 administered. The actual percent peptide content of Compound #8114 administered can be determined by such well known procedures as elemental analysis or amino acid analysis.

In Table 6, Compound #8114 is shown to promote the release and elevation of growth hormone levels in the blood of beef calves to which the compound has been administered. The increase in blood growth hormone levels is also shown to be related to the dosage of Compound #8114.

EXAMPLE 5

In Vivo Growth Hormone Release Study -Cows

Four non-lactating Holstein cows (mean body weight 543 kg) were housed outside in pasture and brought into the large animal laboratory for experimental studies in conventional stanchions. Cow diet was hay, grass and 1x/day 5 lbs. of Omolene (wheat, oats, corn, soybean, molasses with vitamins and trace minerals) - purina. Cows were in the large animal laboratory and off grass for 1-1.5 hours before initiation of experiments. Catheters were inserted into the jugular vein for withdrawal of blood samples and IV injections of peptides. Fifteen to twenty ml of saline was flushed through the catheter after each blood drawing and a slow i.v. drip of saline was used to keep the blood from clotting in the catheter. Ten ml blood samples were collected between 9AM and 2PM at $-40$, $-30$, $-10$, $0$, $+5$, $+10$, $+15$, $+20$, $+25$, $+30$, $+40$, $+60$, $+90$, $+120$, $+150$, $+180$. Normal saline with 0.1% gelatin or peptides dissolved in 0.1% gelatin saline was injected IV through the catheter at 0 time to the unanesthetized cows. The saline/peptide was infused over a 3 minute period in a 5.0 volume. The blood was allowed to clot, centrifuged and the serum separated from the clot. Serum was kept frozen until the day of sampling for radioimmunoassay (RIA) of growth hormone. Serum GH was measured by RIA with reagents provided by the NIADDK. The GH levels are reported in terms of ng/ml of a bovine GH reference preparation, NIH-GH-B18, which is equivalent to 3.2 IU/mg. Data is recorded as the mean± the standard error of the mean (SEM). Statistical analysis was performed with the Student's t-test.

Controls animals (to which no growth hormone releasing compound was administered) showed a growth hormone level of 0.17 +/−0.19 ng/ml, while animals to which 3 μg per kg body weight of Compound #8114 had been administered has a blood serum growth hormone level of 8.60 +/−2.50, thus demonstrating a significant enhancement of growth hormone levels upon administration of Compound #8114.

The invention has been described in detail with particular reference to preferred embodiments thereof, but it will be understood that variations and modifications can be effected within the spirit and scope of the invention.

We claim:

1. A polypeptide capable of promoting the release and elevation of growth hormone levels in the blood of a recipient animal, wherein said polypeptide is selected from the group consisting of polypeptides defined by the generic structure:

X-AA1-AA2-AA3-AA4-Trp-AA6-AA7-Z, wherein X is selected from the group consisting of H, DOPA, Lys, Phe, Tyr, Cys, Tyr-DAla-Phe-Gly, Tyr-DAla-Gly-Phe and Tyr-Ala-Gly-Thr:

AA1 is selected from the group consisting of:
all naturally occurring L-amino acids,
Met (0). DOPA and
Abu:

AA2 is selected from the group consisting of His and 3(NMe)His (i.e., wherein the imidazole ring is methylated at the 3-position):

AA3 is selected from the group consisting of DTrp, 5-fluoro-D or D/LTrp: 6-fluoro-D or D/LTrp (i.e., wherein the indole ring is fluorinated at the 5- or 6-position), (formyl)DTrp (i.e., DTrp which is formylated at the indole nitrogen), and *XTrp, wherein *XTrp is selected from the group consisting of the N-monomethylated DTrp isomers (i.e., $(N^\alpha Me)DTrp$ and (indole NMe)DTrp:

AA4 is selected from the group consisting of Ala, Gly and Ser:

AA6 is selected from the group consisting of DPhe and (NMe)DPhe:

AA7 is selected from the group consisting of Arg, iLys, Lys and Orn: and

Z represents the C terminal end group of said polypeptide or the C terminal amino acid (s) plus end group, wherein Z is selected from the group consisting of —CONH₂, —COOH, —COOR, —CONHR, —CONR₂, —CH₂OH and —CH₂OR, wherein R is an alkyl group having 1-6 carbon atoms or an aromatic ring having up to 12 carbon atoms: and wherein Z is alternatively selected from the group consisting of —Gly —Z', —Met—Z'-,—Lys—Z', —Cys—Z'(when a Cya moiety is also present in the 1 position of the polypeptide (i.e., X or AA1 is Cys), the resulting peptide can exist in the linear form or in the cyclic form), —Gly—Tyr—Z', and —Ala—Tyr—Z', wherein Z' is selected from the group consisting of —CONH₂, —COOH, —CONHR, —COOR, —CONR₂, —CH₂OH, and —CH₂OR, wherein R in as defined above:

and organic or inorganic addition salts of any of said polypeptides:

wherein the amino acid residue abbreviations used are in accordance with the standard peptide nomenclature:

| | |
|---|---|
| Gly = | Glycine |
| Tyr = | L-Tyrosine |
| Ile = | L-Isoleucine |
| Glu = | L-Glutamic Acid |
| Thr = | L-Threonine |
| Phe = | L-Phenylalanine |
| Ala = | L-Alanine |
| Lys = | L-Lysine |
| Asp = | L-Aspartic Acid |
| Cys = | L-Cysteine |
| Arg = | L-Arginine |
| Gln = | L-Glutamine |
| Pro = | L-Proline |
| Leu = | L-Leucine |
| Met = | L-Methionine |
| Ser = | L-Serine |
| Asn = | L-Asparagine |
| His = | L-Histidine |
| Trp = | L-Tryptophan |
| Val = | L-Valine |
| DOPA = | 3,4-L-Dihydroxyphenylalanine |
| Met(O) = | L-Methionine sulfoxide |
| iLys = | $N^\epsilon$—Isopropyl-L-lysine |
| Abu = | alpha-L-Aminobutyric acid |
| Orn = | L-Ornithine |
| Pal = | 3-Pyridyl-L-alanine |
| Pgl = | L-Phenylglycine |
| (beta)Ala = | beta alanine (i.e., 3-aminopropanoic acid) |

All three letter amino acid abbreviations preceded by a "D" indicate the D-configuration of the amino acid residue.

2. A polypeptide in accordance with claim 1, wherein said polypeptide is selected from the group consisting of:

Ala-His-DTrp-Ala-Trp-DPhe-Lys-Gly-Tyr-Z';
Ala-His-(formyl)DTrp-Ala-Trp-DPhe-Lys-Z'(DTrp is formylated at the indole nitrogen);
Ala-His-DTrp-Ser-Trp-DPhe-Lys-Z';
Cys-Ala-His-DTrp-Ala-Trp-DPhe-Lys-Cys-Z'(cyclic disulfide);
Cys-Ala-His-DTrp-Ala-Trp-DPhe-Lys-Cys-Z'(free dithiol);
DOPA-Ala-His-DTrp-Ala-Trp-DPhe-Lys-Z';
His-DTrp-Ala-Trp-DPhe-Lys-Ala-Tyr-Z';
Lys-Ala-His-DTrp-Ala-Trp-DPhe-Lys-Z';
Phe-Ala-His-DTrp-Ala-Trp-DPhe-Lys-Z';
Tyr-Ala-Gly-Thr-Ala-His-DTrp-Ala-Trp-DPhe-Lys-Z';
Tyr-Ala-His-DTrp-Ala-Trp-DPhe-Lys-Z';
Tyr-DAla-Phe-Gly-Ala-His-DTrp-Ala-Trp-DPhe-Lys-Z';
Tyr-DAla-Gly-Phe-Ala-His-DTrp-Ala-Trp-DPhe-Lys-Z';
Ala-His-DTrp-Ala-Trp-DPhe-iLys-NH₂;
Ala-His-DTrp-Ala-Trp-(NMe)DPhe-Lys-NH₂;
Ala-His-*XTrp*-Ala-Trp-DPhe-Lys-Z'(*XTrp* is selected from the group consisting of 5-fluoro-D or D/LTrp; 6-fluoro-D or D/LTrp (i.e., wherein the indole ring is fluorinated at the 5- or 6-position), and the N-monomethylated DTrp isomers, i.e., (NαMe)DTrp, and (indole NMe)DTrp); AAl-His-DTrp-Ala-Trp-DPhe-Lys-Z';

wherein AA1 is selected from the group consisting of:
all naturally occurring L-amino acids,
Met(O),
DOPA and
Abu;

wherein Z' and R are as defined above; and
organic or inorganic addition salts of any of said polypeptides.

3. A polypeptide in accordance with claim 1 wherein said polypeptide is selected from the group consisting of:

DOPA-Ala-His-DTrp-Ala-Trp-DPhe-Lys-NH₂;
His-DTrp-Ala-Trp-DPhe-Lys-Ala-Tyr-NH₂;
Lys-Ala-His-DTrp-Ala-Trp-DPhe-Lys-NH₂;
Tyr-Ala-His-DTrp-Ala-Trp-DPhe-Lys-NH₂;
Phe-Ala-His-DTrp-Ala-Trp-DPhe-Lys-NH₂;
Ala-His-DTrp-Ala-Trp-DPhe-iLys-NH₂;
Ala-His-DTrp-Ala-Trp-(NMe)DPhe-Lys-NH₂;
Ala-His-DTrp-Ala-Trp-DPhe-Lys (as the free carboxylate);
AAl-His-DTrp-Ala-Trp-DPhe-Lys-NH₂; wherein AAlis selected from the group consisting of:
all naturally occurring L-amino acids.
DOPA,
Met(O) and
Abu, and
organic or inorganic addition salts of any of said polypeptides.

4. Method of promoting the release and elevation of blood growth hormone levels in animals by administering thereto an effective amount of at least one of the polypeptides set forth in claim 1.

5. Method of promoting the release and elevation of blood growth hormone levels in animals by administering thereto an effective amount of at least one of the polypeptides set forth in claim 2.

6. Method of promoting the release and elevation of blood growth hormone levels in animals by administering thereto an effective amount of at least one of the polypeptides set forth in claim 3.

* * * * *